United States Patent [19]

Norris

[11] 4,136,406

[45] Jan. 30, 1979

[54] INTRAOCULAR LENS WITH ATTACHED DISPOSABLE INSTRUMENT

[76] Inventor: John W. Norris, 7927 Johnson St., Pembroke Pines, Fla. 33024

[21] Appl. No.: 817,195

[22] Filed: Jul. 20, 1977

[51] Int. Cl.² .......................... A61F 1/16; A61F 1/24; A61F 9/0

[52] U.S. Cl. ..................................... 3/13; 128/303 R

[58] Field of Search .......................... 3/13; 128/303 R

[56] References Cited

U.S. PATENT DOCUMENTS

| 3,906,551 | 9/1975 | Otter | 3/13 |
|---|---|---|---|
| 3,991,426 | 11/1976 | Flom et al. | 3/13 |
| 3,996,626 | 12/1976 | Richards et al. | 3/13 |
| 4,047,532 | 9/1977 | Phillips et al. | 128/303 R |

Primary Examiner—Ronald L. Frinks
Attorney, Agent, or Firm—Oltman and Flynn

[57] ABSTRACT

A disposable tool is disclosed for use in intraocular implantation of a pseudophakos (artificial intraocular lens) having a lens, posterior iris clips and an anterior fastening clasp for insertion in an iridectomy. The tool comprises:

a manually manipulatable tool body for engagement with one of the iris clips;

a slide movably connected to the tool body for releasably engaging the fastening clasp;

and a fastener for detachably affixing the pseudophakos to the tool body.

11 Claims, 12 Drawing Figures

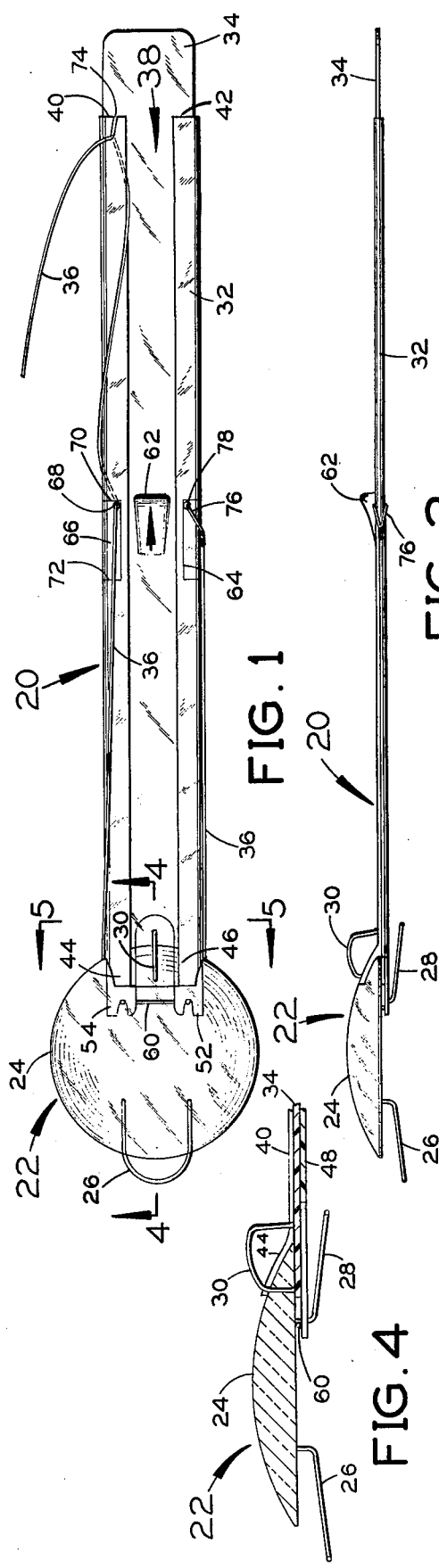

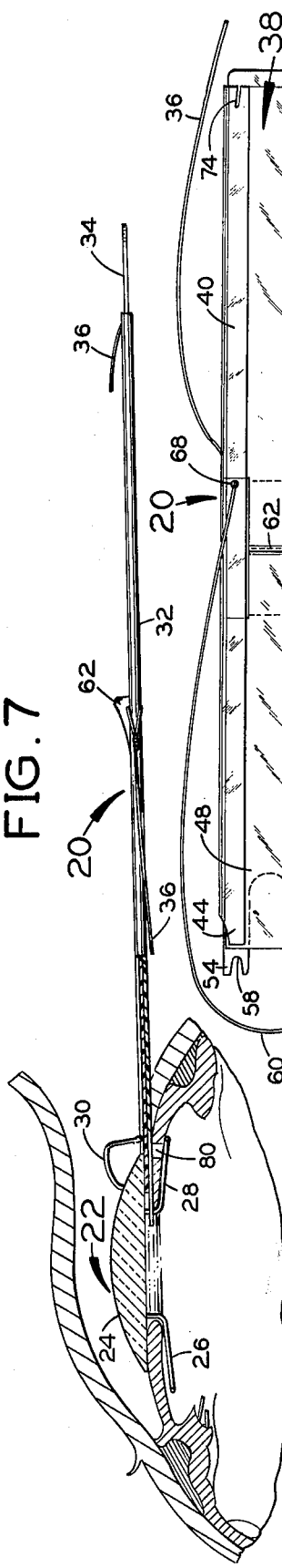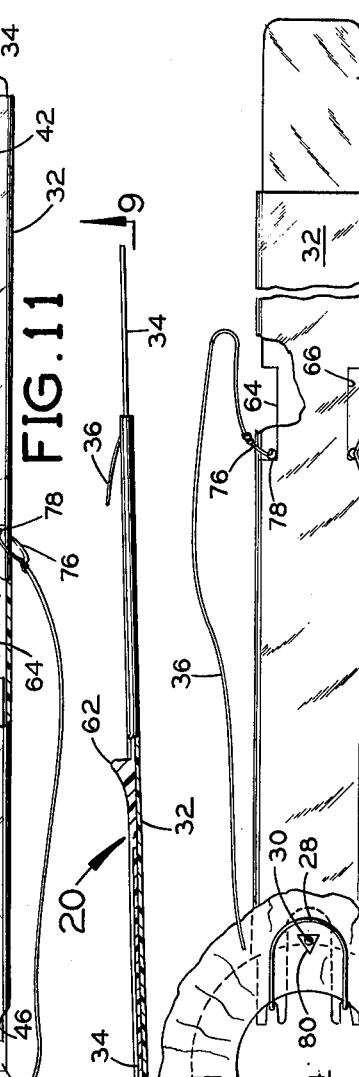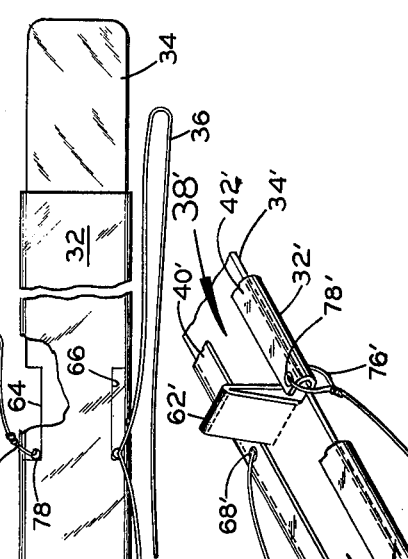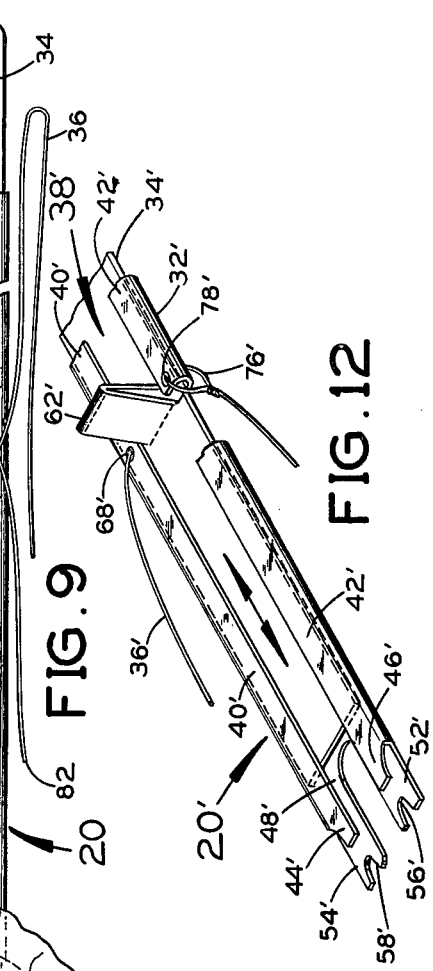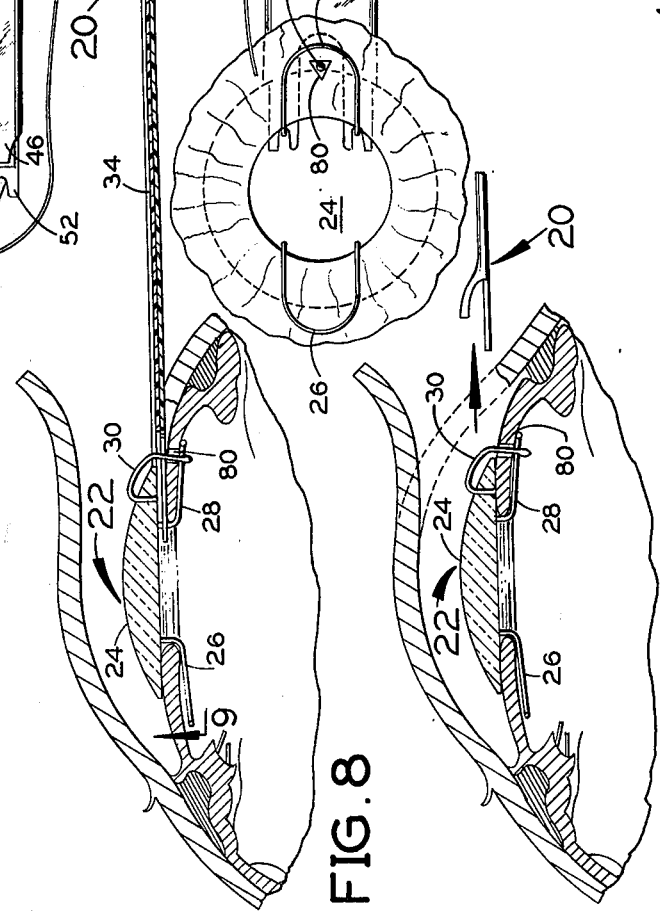

INTRAOCULAR LENS WITH ATTACHED DISPOSABLE INSTRUMENT

BACKGROUND OF THE INVENTION

A pseudophakos is an artificial, intraocular lens which is implanted in the eye to correct aphakia. U.S. Pat. No. 3,996,626 describes a certain type of pseudophakos having a lens, posterior iris clips, and a fastening clasp. Reference is made to that patent for information on the construction of such a pseudophakos. Tools for use in implanting pseudophakoi are known generally, but they have been awkard and relatively expensive. An example of such a tool is described for example in U.S. Pat. No. 3,991,426.

SUMMARY OF THE INVENTION

The invention provides a tool or instrument which can be used in implanting a pseudophakos and then thrown away. It can be placed in a sterile package with the pseudophakos when supplied to the surgeon so that it does not require sterilization before use. It comprises a tool body, a slide and a fastener. The slide is preferably a flat strip, and the tool body then is also a flat strip partially wrapped about the slide strip. The fastener is preferably a bridle line retaining the pseudophakos in engagement with the body strip.

It is an object of the present invention to so simplify the construction of a lens implanting tool as to make it possible to dispose of the tool after use in surgery.

Another object of the invention is to prepackage a lens implanting tool in a sterile package which eliminates the need for sterilizing the tool before use in surgery.

Other objects of this invention will appear from the following description and appended claims, reference being had to the accompanying drawings forming a part of this specification wherein like reference characters designate corresponding parts in the several views.

BRIEF DESCRIPTION OF THE DRAWINGS

FIG. 1 is a top plan view of a tool in accordance with one embodiment of the invention affixed to an artificial, intraocular lens;

FIG. 2 is a side elevational view of the tool and lens;

FIG. 3 is a bottom plan view of the tool and lens;

FIG. 4 is a sectional view taken along line 4—4 of FIG. 1;

FIG. 5 is a cross sectional view taken along line 5—5 of FIG. 1;

FIG. 6 is a diagramatic view illustrating the use of the tool in implanting the lens;

FIG. 7 is another diagramatic view showing a second step in the implantation of a lens;

FIG. 8 is a diagramatic view illustrating the retraction of a slide of the tool to allow a fastener clasp for the lens to automatically insert through an iridectomy;

FIG. 9 is a fragmentary cross sectional view along line 9—9 of FIG. 8;

FIG. 10 is a diagramatic view illustrating the removal of the tool;

FIG. 11 is a top plan view of the tool alone; and

FIG. 12 is a perspective view of a modification of the tool.

Before explaining the disclosed embodiments of the present invention in detail, it is to be understood that the invention is not limited in its application to the details of the particular arrangements shown, since the invention is capable of other embodiments. Also, the terminology used herein is for the purpose of description and not of limitation.

DETAILED DESCRIPTION

The disposable tool 20 is intended to be affixed to a pseudophakos or artificial intraocular lens 22 at the factory where the lens and tool are manufactured so that the lens and tool assembly can be prepackaged in a sterile container or package. The prepackaged lens and tool assembly is supplied to the surgeon in a sterile condition which eliminates any need for sterilization of the tool before use. After use in surgery, the tool is thrown away.

The pseudophakos 22 consists of a lens 24, posterior iris clips 26 and 28, and a pre-formed or bent fastening clasp 30 intended for insertion through an iridectomy during surgery. A lens of this type is described in the aforementioned U.S. Pat. No. 3,996,626 and reference is made to that patent for details of construction of a suitable pseudophakos.

The tool 20 includes a manually manipulatable tool body 32 for engagement with one of the iris clips 28. The tool also includes a slide 34 movably connected to the tool body for releasably engaging the fastening clasp 30, and a fastening means 36 in the form of a bridle line for detachably affixing the pseudophakos 22 to the tool body 32.

The slide 34 is preferably in the form of a generally flat slide strip. The tool body 32 is also preferably in the form of a strip, but the body strip 32 is partially wrapped about the slide strip leaving an open space at 38. The body strip 32 has folded over side portions 40 and 42 grasping or frictionally engaging the slide strip 34, and the side portions 40 and 42 have undercut ends 44 and 46 for engaging the top side of lens 24.

The body strip 32 has a bifurcated end 48 with a recess 50. The projections 52 and 54 at the bifurcated end 48 have recesses 56 and 58 for receiving a loop portion 60 of the bridle line 36. As shown particularly in FIG. 4, the loop portion 60 extends about one of the iris clips 28 to secure the pseudophakos 22 to the bifurcated end 48 of the body strip 32.

The slide strip has an extended position as shown in FIGS. 1-3 wherein it partially covers the recess 50 at the bifurcated end 48 of the body strip 32. Thus, the left end of the slide strip 34 extends under the fastener clasp 30 as shown in FIG. 4 to hold that clasp retracted up out of the way of the iris clip 28 while the pseudophakos 22 is being implanted in an eye. The slide strip 34 may be retracted by simply shifting it to the right as viewed in FIGS. 2-4 to allow the fastener clasp 30 to shift down and automatically insert through an iridectomy as will be further explained. The slide strip 34 preferably has a projection 62 to facilitate retraction of the slide strip, and this may be conveniently done by engaging the projection 62 with the thumb to retract the slide strip 34 to the right.

The slide strip 34 preferably has recesses 64 and 66 at about the mid-point thereof. The bridle line 48 passes through an opening 68 in the body strip 32 at the recess 66 so that the recessed portion of the slide 34 at recess 66 limits the lateral movement of the slide strip 34 by engagement with the line 36 at the opening 68. When the slide strip 34 is all the way to the left as shown in FIG. 1, the projection 70 engages the line 36, and when the slide strip 34 is all the way to the right in a retracted position, the projection 72 engages the line 36 at the opening 68.

The bridle line 36 is detachably inserted in a slot 74 in the side portion 40 of the body strip 32. From there, the line 36 extends around to the bottom of the body strip 32 and passes up through the opening 68 into a space under the slide strip 34. The bridle line then extends around the iris clip 28 and back into the body strip 32 on the other side of the slide strip 34. The line 36 is tied at a knot 76 which passes through another opening 78 in the bottom of the body strip 32.

The body strip 32 and the slide strip 34 are preferably made of transparent plastic. The bridle line 36 is preferably a surgical suture material.

In use, the pseudophakos and tool assembly is manipulated so as to insert the pseudophakos into an incision in the eye in the manner illustrated in FIG. 6. The iris clip 26 has been inserted behind the iris as shown.

In FIG. 7, the other iris clip 28 has been inserted behind the iris. The fastener clasp 30 remains elevated since the slide strip 38 has not yet been retracted.

FIG. 8 illustrates the step of retracting the slide strip 34 so as to allow the fastener clasp 30 to pass through the iridectomy 80 to help prevent luxation.

FIG. 9 illustrates cutting or severing of the bridle line 36 at 82 so that bridle 36 may be removed from the pseudophakos. The tool 20 may then be removed from the pseudophakos as shown in FIG. 10, and the incision may be closed.

FIG. 12 illustrates a modification of the tool wherein the same reference numerals are used for like parts except that a prime designation has been added. The projection 62' is a folded portion of the slide strip 34'. The openings 68' and 78' are formed in the upper side portions 40' and 42' of the body strip 32'. In all other respects, the embodiment of FIG. 12 is identical to the embodiment of FIGS. 1-11.

Having thus described my invention, I claim:

1. A disposable tool for intraocularly implanting a pseudophakos having a lens, posterior iris clips and an anterior fastening clasp for insertion in an iridectomy, said tool comprising:
   a manually manipulatable tool body for engagement with one of said iris clips;
   slide means movably connected to said tool body for releaseably engaging said fastening clasp;
   and fastening means for detachably affixing said pseudophakos to said tool body.

2. The tool as claimed in claim 1 in which:
   said slide means comprises a generally flat slide strip;
   and said tool body comprises a body strip partially wrapped about said slide strip to permit telescopic movement of said slide strip.

3. The tool as claimed in claim 2 in which:
   said body strip has a bifurcated end for engaging said iris clip.

4. The tool as claimed in claim 3 in which:
   said slide strip has a position wherein one end thereof at least partially covers said bifurcated end of said body strip;
   and said slide strip is retractable from said position to open said bifurcated end.

5. The tool as claimed in claim 4 in which:
   said body strip has folded over side portions grasping said slide strip; and
   said side portions have undercut ends for engaging said lens.

6. The tool as claimed in claim 1 wherein:
   said fastening means comprises a bridle line.

7. The tool as claimed in claim 6 in which:
   said slide means comprises a generally flat slide strip;
   and said body comprises a generally flat body strip partially wrapped about said slide strip;
   said line being detachably affixed to said body strip.

8. The tool as claimed in claim 7 in which:
   said body strip has a bifurcated end for engaging said iris clip;
   and said line provides a loop at said bifurcated end.

9. The tool as claimed in claim 8 in which:
   said slide strip has a position wherein one end thereof at least partially covers said bifurcated end of said body strip;
   and said slide strip is retractable from said position to open said bifurcated end.

10. The tool as claimed in claim 9 in which:
    said line passes through a portion of said body strip;
    and said slide strip has a recessed portion cooperating with said line at said body portion to limit the movement of said slide strip.

11. A disposable tool as claimed in claim 1 wherein said tool is attached to said pseudophakos.

* * * * *